United States Patent [19]
Melanson et al.

[11] Patent Number: 4,687,904
[45] Date of Patent: Aug. 18, 1987

[54] ELECTRICALLY HEATED INSECTICIDE DISPENSER

[75] Inventors: Lionel J. Melanson, Casco, Me.; Nabil Kamal, Hampton, N.H.

[73] Assignee: GTE Products Corporation, Stamford, Conn.

[21] Appl. No.: 892,615

[22] Filed: Aug. 4, 1986

[51] Int. Cl.[4] .............................................. H05B 1/02
[52] U.S. Cl. .................................... 219/271; 219/275; 239/136; 422/305; 43/129
[58] Field of Search .............. 219/271, 272, 273, 274, 219/275, 276; 422/305, 306, 125; 239/135, 136, 44, 47, 51.5, 53, 54, 55, 56, 57, 58, 59, 60; 43/129

[56] References Cited

U.S. PATENT DOCUMENTS

| 1,102,424 | 7/1914 | McNabb | 219/272 |
| 1,908,054 | 5/1933 | Riley | 219/275 |
| 2,612,432 | 9/1952 | Boddy | 219/272 |
| 2,660,828 | 12/1953 | Abrams | 219/272 |
| 3,366,775 | 1/1968 | Mycue | 219/272 |
| 4,163,038 | 7/1979 | Nishimura | 422/305 |
| 4,571,485 | 2/1986 | Spector | 239/136 |

FOREIGN PATENT DOCUMENTS 1479904 5/1967 France ................................. 43/129

Primary Examiner—E. A. Goldberg
Assistant Examiner—Teresa J. Walberg
Attorney, Agent, or Firm—James Theodosopoulos

[57] ABSTRACT

An insecticide dispenser capable of setting off a charge of insecticide to fumigate a room and then automatically shutting itself off before the completion of the dispensing of the charge of the insecticide, whereby the dispenser can be safely left unattended during the fumigation of a room. The dispenser includes a container for the insecticide and a fusible member that will break during the volatilization of the insecticide thereby to break the electrical circuit and turn off the power supply.

6 Claims, 2 Drawing Figures

ELECTRICALLY HEATED INSECTICIDE DISPENSER

FIELD OF THE INVENTION

The present invention relates to electrically heated insecticide dispensers for rooms and particularly to those which are adapted to disperse a charge of insecticide from a container which is to be used only once and in which the insecticide dispenser will shut itself off automatically when the charge has been dispensed.

SUMMARY OF THE PRIOR ART

Insecticide dispensers are well known to the art and devices have previously been introduced which are adapted to dispense insecticides into a room when a container is heated. For example, the United States patent to van Lit, U.S. Pat. No. 4,391,781, discloses a resistance heating device that can be utilized with a mat of paper that has been impregnated with an insecticide. The paper strip is urged against the resistance heater so that when the current is turned on, it will dispense the insecticide that is held on the paper. The paper is held against the resistance heating element by a clamp arm that presses the mat against the surface. A depressible lever engages the clamp arm and moves it away from the heating surface thereby releasing the paper strip to facilitate its replacement. In the van Lit patent, however, no disclosure is made of a container of insecticide and the limiting of the dispensing is controlled by the amount of vaporizable material that is held within the paper. No attempt is made in the van Lit patent to shut the resistance heating element off when the vaporizable material has been fully dispensed.

Since the present invention relates to dispensers for insecticides that utilize cannisters which are to be used only once, it is necessary to turn off the resistance heating element when the vaporizable material is fully dispersed into the room. The usual approach for dispensing such vaporizable material is to initiate the vaporization and then quickly leave the room where the dispenser has been disposed. The room is not reentered until quite a while later, when the vapor has settled and is not toxic to the person who is doing the fumigation. If the resistance heater were left on during the entire waiting period, a possibility exists that the dispenser could overheat and cause a fire while it is unattended. Thus, while the van Lit patent may be appropriate for dispensing certain small quantities of volatilizable material, we have found that it is inappropriate for large scale fumigation of entire rooms.

The United States patent to Lin, U.S. Pat. No. 4,202,472 discloses the use of a device for bagging trash and simultaneously dispensing insecticides or repellents. The insecticide or repellent is slowly dispensed into the trash to prevent the breeding of micro-organisms. The device does not involve the use of electrical heating for the container and dispenser and thus is not adaptable for use for fumigating a room. The United States patent to Beacham, U.S. Pat. No. 4,316,279, discloses a combined container and dispenser for dispensing a volatile product such as an air freshener or insecticide. The invention involves a continuous, low rate dispensing of the volatile product in an ambient atmosphere and is especially not related to the sudden volatilization of large quantities of insecticides such as are contemplated in the present invention. The invention of Beacham is designed to be unobtrusively stuck or hung to a hidden surface so that it is not normally observable by persons nearby whereby the vaporizable material will slowly disperse into the room where it is disposed.

Automated aerosol mist dispensers are disclosed in the United States patent to Mettler, U.S. Pat. No. 3,974,941. Patentee discloses a device for injecting short bursts of an atomized liquid such as air fresheners, medicines or insecticides at desired intervals from a spray nozzle in communication with a conventional aerosol can that contains a fluid under pressure. With Mettler's invention, an automated aerosol mist dispenser is disclosed that affords a secure interconnection between the pressurized can of fluid and the control valve mechanism and which is safe against undue leakage, even at relatively high temperatures owing to the provision of a balancing piston feature. No concept, however, is disclosed by Mettler for dispensing a large volume of insecticide into a room in a single charge through the use of a controlled resistance heating element.

United States patents to Scarpa, U.S. Pat. Nos. 3,151,785, and to Kare, 3,466,789, involve the use of liquid insecticide dispensers in which the rate of liquid that is being dispensed is controlled though slow dripping of the liquid and subsequent atmospheric volatilization. While Kare may disclose a single dose dispenser for the insecticide, no disclosure is made of electrically heating the dispenser to volatilize its contents.

SUMMARY OF THE INVENTION

According to the present invention, we have discovered an insecticide dispenser that can be electrically heated to dispense the insecticide and then shut itself off automatically. The heat radiated from a PTC heater (as will be described later) initiates a self-sustaining, exothermic chemical reaction in the insecticide-carrier mixture that is held in a container. The heat from the chemical reaction and current passing through a fusible lead-in wire will melt the lead-in wire and break the electrical circuit after the reaction is initiated. The container is adapted to be part of the electrical circuit and its placement in a holder completes the circuit. When the lead-in wire breaks, the circuit will break, thereby preventing the dispenser from overheating while it is unattended.

Our insecticide dispenser utilizes the PTC (positive temperature coefficient ceramic) heater to initiate the chemical reaction. The PTC heater heats the insecticide container to a precise temperature and maintains that temperature over a period of time sufficient to initiate the reaction.

When the insecticide is volatilized, or during the volatilization, the lead-in wire will fuse and open the electric circuit leading to the PTC heater and the heating will be discontinued. The container in which the insecticide is disposed can be used only once thereby preventing the possibility of injuring people through subsequent uses or with materials that are not designed for it. Moreover, as stated above, the utilization of the dispenser of the present invention involves a person setting up the device and then turning on the power to commence the volatilization of the insecticide. When the heating has commenced, the fumigator promptly leaves the room in which the action has been initiated and closes the door, thereby containing the insecticide within the room and allowing it to do its work. The door is not opened for a significant amount of time so as to prevent poisoning the fumigator. Since it is not desirable to continue heating the container that holds the insecticide for all of the time the fumigator is out of the room because of the possibility of overheating or fire, the dispenser of the present invention is designed to turn itself off by breaking the electrical circuit thereby turning it off and eliminating these possibilities.

In accordance with the invention, the cannister is disposed upon the PTC heater and is made part of the circuit. When the cannister is disposed upon the PTC heater, electrical contact is made with the other side of the power supply through an electrical contact on the housing. The fusible member is disposed within the cannister. One end of the fusible member is electrically connected to the outside of the container but insulated therefrom. Its other end is attached to and electrically connected to the container and arranged so that the heat from the vaporizing insecticide and the current passing therethrough will gradually melt it. When the fusible member is melted, the circuit will be broken and the PTC heater will be turned off.

PTC heaters have been in use for many years. Such heaters offer several operating advantages over conventional resistance heating elements in the heating of containers of insecticides. They generally are flat and made from doped barium titanate ceramics which have a sharp positive temperature coefficient of resistance. The PTC ceramics are designed such that below a critical temperature, the resistance of the ceramic remains at low value and is essentially constant. When a particular temperature is reached, a crystalline phase change takes place in the ceramic and this abrupt change in crystal structure is accompanied by a sharp increase in the resistance at the crystalline grain boundaries. The result of this crystalline change is an increase in the heater resistance of several orders of magnitude over a very small temperature change. A barium titanate heater with a room temperature of resistance of 3.0 ohms will increase to 1000 ohms or more during the crystalline phase change. The temperature at which the crystalline phase change takes place can be adjusted in the PTC manufacturing process through the use of appropriate chemical additives and can be varied between 60 and 180 degrees centigrade.

When energized with a suitable voltage by applying current to the opposite side of it, the PTC ceramic rapidly heats up to a predetermined operating temperature and then "locks in" at this temperature. This rapid warm up is due to the initial low resistance of the PTC ceramic heater which results in an internal high power input of the heater. The "lock in" is due to the abrupt increase in resistance which causes generated power to be reduced until it equals dissipated power. At this point, a thermal equilibrium is achieved and the PTC heater self regulates itself at that temperature.

In the self regulating mode, the container will continue to be heated at the predetermined temperature which is substantially the same as the vaporization point of the insecticide and about the same as the melting point of the fusible member. In this way, the fusible member will melt after the vaporization has commenced but before it is completed thereby to break the circuit and prevent the container from overheating. A simple mechanism is provided for turning off the dispenser without someone being present.

DESCRIPTION OF THE DRAWINGS

In FIG. 1, the heater has not yet been turned on and thus the fusible wire is still intact.

In FIG. 2 the insecticide has been volatilized and the power to the dispenser has been turned off since the wire has been broken.

DESCRIPTION OF THE PREFERRED EMBODIMENTS

Figure 1:
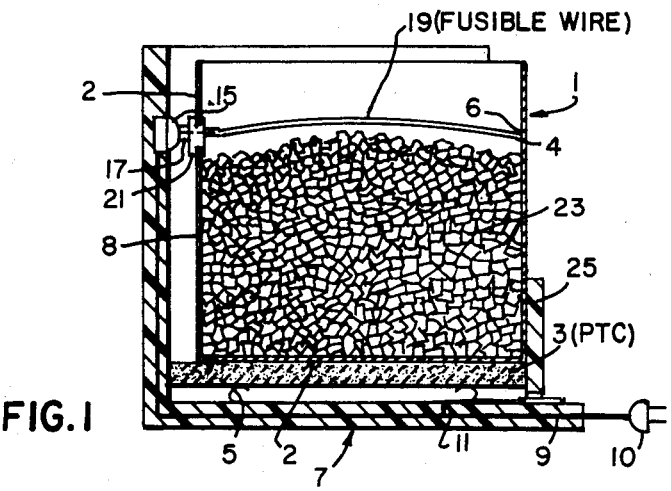
FIGS. 1 and 2 are cross sectional views of an insecticide dispenser with a conductive container disposed within a housing.

In FIG. 1, a container 1 is shown with its bottom wall 2 disposed upon a PTC heater 3. The PTC heater 3 rests on, and is in electrical contact with contacts 5. Container 1 has a fusible wire 19 disposed between one side wall and another. Fusible member 19 is attached to side wall 4 at connection 6 so as to provide an electrical contact, as will be described later. Fusible member 19 preferably spans the container 1 and extends through side wall 8 but is insulated therefrom by insulator 21. A contact button 17 is disposed at the distal end of fusible wire 19 and forms an exposed electrical contact for the circuit. An exposed contact member 15 is disposed upon side wall 8 of housing 7 and is arranged to form an electrical connection with contact button 17, thereby to complete the circuit.

The PTC heater 3 will initiate a chemical reaction within a mass of insecticide 23. The mass of insecticide contains a mixture of the active ingredient (the insecticide) dispersed within a carrier. When the heating commences in the container 1, a chemical reaction begins with the carrier and copious volumes of smoke are given off. The chemical reaction is selfsustaining, that is additional heat need not be added to it when the reaction begins. The reaction will continue until all of the carrier is reacted and the insecticide is volatilized together with the smoke that is produced. Since the resistivity of the fusible member 19 is higher than that of the container 1, the fusible member 19 will eventually melt and break the circuit that has been established between the contact member 15 and the connection 6. When the connection is broken, no further current passes through the container 1 to provide a complete circuit to the PTC heater 3 through the bottom wall 2. The PTC heater will then be shut off and the chemical reaction will continue until the charge of insecticide is completely volatilized. In a preferred embodiment, the fusible member 19 is a length of 60-40 solder which is sufficiently thick to withstand the temperatures produced by the initiation of the chemical reaction within the charge 23. It is thin enough, however, to eventually melt itself thereby to break the circuit. Such parameters can easily be determined by those skilled in the art so as to adjust for sizes of the container and the heat produced by the chemical reaction. The fusible member 19, however, must be sufficiently thin so that it will break the circuit before the conclusion of the volatilization of the charge of insecticide 23.

The container 1 is preferably seated upon the PTC heater 3 as mentioned above. A portion of the side wall of the housing 7 of the insecticide dispenser is cut away thereby to form a receiving wall 25 which can enable the fumigator to insert or remove the cannister 1 from the dispenser.

The base of the housing 7 provides a receptacle for an electrical wire 9 which terminates at one end with a conventional plug 10. One side 11 of the wire 9 is connected to the electrical contact 5 and the other side extends through the housing 7 to reach the contact member 15.

Figure 2:
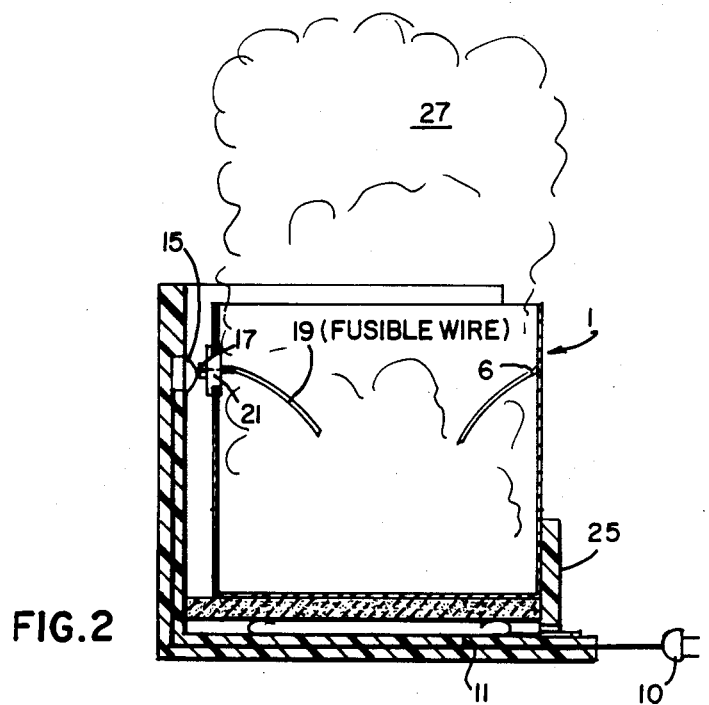

As shown in FIG. 2, when the insecticide cloud 27 has been formed and the insecticide has been dispersed into the room, the fusible wire 19 will break, thereby breaking the circuit between the container 1 and the contact member 15 through the contact button 17. The container 1 cannot be reused because of the difficulty of reuniting the fusible member 19 or installing a new fusible member to the side wall of the container.

It is apparent that modifications and changes may be made within the spirit and scope of the present invention. It is our intention, however, only to be limited by the scope of the appended claims.

As our invention we claim:

1. An insecticide dispenser for a room, said dispenser comprising:

a housing and an electrically conductive, nonreuseable container disposed in said housing, said container being disposed upon a resistance heating means and adapted to receive a charge of an insecticide dispersed within a solid carrier, said charge requiring the application of heat to initiate a chemical reaction which produces the volatilization of the insecticide; and first means connecting said container to one side of a power supply; and second means connecting said container to the other side of said power supply, said second means including an electrically conductive fusible means, electrically connected at one end to said container and removably connected at its other end to an electrical contact disposed on said housing, said fusible means being electrically insulated from said container at all points except where it is connected to said container, whereby said fusible means can complete the circuit to the resistance heating means and initiate the chemical reaction in the charge of insecticide; and said fusible means being adapted to break at a predetermined point after said chemical reaction has been initiated whereby to discontinue the electrical heating to said charge.

2. The dispenser according to claim 1 wherein said resistance heating means is a PTC heater, one side of which is connected to said one side of said power supply and the other side of which is connected to said other side of power supply through said fusible means that is connected to said container.

3. The dispenser according to claim 2 wherein the fusible means is a section of solder wire.

4. The dispenser according to claim 2 wherein the container has a flat bottom, arranged to be disposed upon a flat PTC heater.

5. The dispenser according to claim 2 wherein an insulator is disposed on the side wall of said container and said fusible means extends through said insulator to the ouside thereof to an electrical contact surface.

6. The dispenser according to claim 5 wherein a contact is disposed on said housing and arranged to engage said contact surface on said container.

* * * * *